United States Patent [19]

Yoshihama et al.

[11] Patent Number: 5,079,377
[45] Date of Patent: Jan. 7, 1992

[54] NOVEL ANDROST-4-ENE-3,17-DIONE DERIVATIVES AND METHOD FOR PREPARING SAME

[75] Inventors: Makoto Yoshihama, Utsunomiya; Koji Tamura, Shimotsuga; Nobuo Miyata, Utsunomiya; Shoji Nakayama, Utsunomiya; Masamichi Nakakoshi, Utsunomiya, all of Japan

[73] Assignee: Snow Brand Milk Products Co., Ltd., Sapporo, Japan

[21] Appl. No.: 555,691

[22] Filed: Jul. 23, 1990

Related U.S. Application Data

[62] Division of Ser. No. 279,596, filed on PCT/JP88/00114, Feb. 5, 1988, Pat. No. 4,975,368.

[30] Foreign Application Priority Data

Feb. 6, 1987 [JP] Japan ............................ 62-24594
Feb. 6, 1987 [JP] Japan ............................ 62-24595
Feb. 6, 1987 [JP] Japan ............................ 62-24598
Feb. 6, 1987 [JP] Japan ............................ 62-24599

[51] Int. Cl.$^5$ ............................................. C07J 1/00
[52] U.S. Cl. ............................................... 552/615
[58] Field of Search ................................. 552/615

[56] References Cited

PUBLICATIONS

Gabinskaya, Khim–Farm. Zh 19, 76, 1980.

*Primary Examiner*—Robert Gerstl
*Attorney, Agent, or Firm*—Millen, White & Zelano

[57] ABSTRACT

Novel androst-4-ene-3,17-dione derivatives are disclosed. The group of these compounds has biological activities, in particular, the inhibiting activity on human placenta-derived estrogen-synthesizing enzyme. Therefore these compounds are expected to be utilized in the field of medical care, particularly as anticancer drugs.

7 Claims, 17 Drawing Sheets

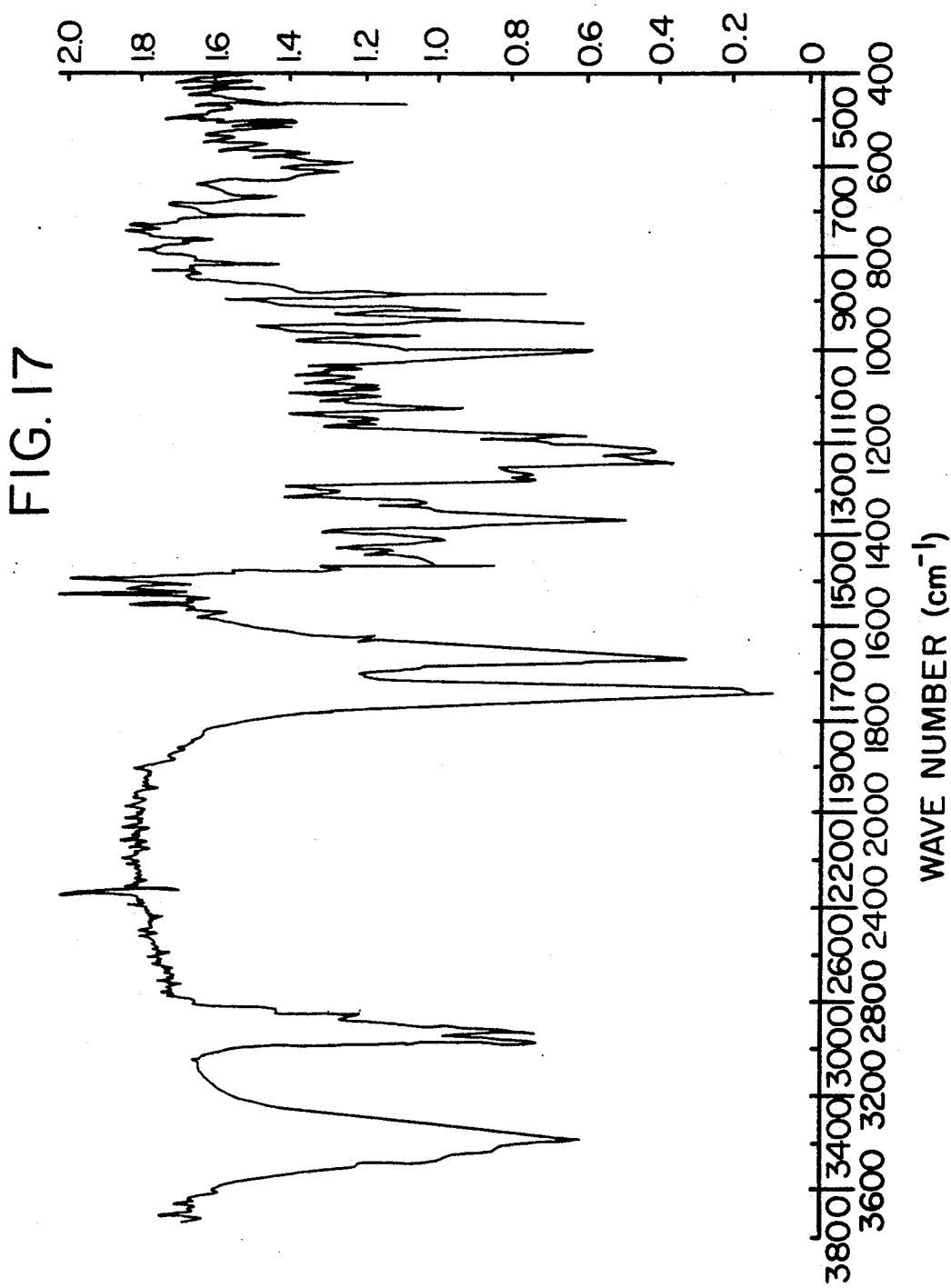

NOVEL ANDROST-4-ENE-3,17-DIONE DERIVATIVES AND METHOD FOR PREPARING SAME

This is a division of application Ser. No. 07/279,596, filed Sept. 26, 1988, now U.S. Pat. No. 4,975,368.

TECHNICAL FIELD

This invention relates to androstene derivatives having biological activities such as inhibiting activity against estrogen-synthesizing enzyme (aromatase) derived from human placenta. These compounds are expected to be used in the field of medicine.

In addition, it has been found that a part of the derivatives of this invention has also growth-inhibiting activity against human mammary cancer cells (MCF-7). Therefore these compounds are also expected to be utilized as anticancer drugs.

BACKGROUND ART

A variety of androstene derivatives has already been found to date and many of them have been known to exhibit various biological activities. However, the androstene derivatives of this invention are a novel compounds, and hence the biological activities thereof heretofore was unknown.

DISCLOSURE OF INVENTION

The present inventors have researched the action of microorganisms belonging to *Acremonium sp.*, e.g. a strain of mold fungi, in a substrate of androst-4-ene-3,17-dione which is a known androgen. In this invention, as a result, it has been found that two types of novel androstene derivatives are produced.

The present inventors have further subjected one of the derivatives produced above to a reaction in the presence of a specific catalyst. Consequently, it has been found that another androstene derivative having similar biological activities can be obtained. It has also been found that the specific functional group of the same derivative used for the reaction can be substituted with the acyl group to give new derivatives having similar biological activities.

The androstene derivatives of this invention are specified in claim 1, and representative examples of these derivatives have the following chemical names.

Androst-4-ene-3,6,17-trione-14α-ol
Androst-4-ene-3,17-dione-6β,11α-diol
Androst-4-ene-3,17-dione-6β,14α-diol
Androst-4-ene-3,17-dione-6β-acetoxy-14α-ol
Androst-4-ene-3,17-dione-6β-propionyloxy-14α-ol
Androst-4-ene-3,17-dione-6β-isohutyryloxy-14α-ol
Androst-4-ene-3,17-dione-6β-trimethylacetoxy-14α-ol

BRIEF DESCRIPTION OF DRAWINGS

FIG. 1 illustrates an ultraviolet (UV) absorption spectrum. FIG. 2 is a EI mass spectrum. FIG. 3 shows an infrared (IR) absorption spectrum.

FIG. 4 illustrates an IR absorption spectrum. FIG. 5 shows a proton nuclear magnetic resonance (NMR) spectrum. FIG. 6 illustrates a 13C-NMR spectrum.

FIG. 7 illustrates the growth-inhibiting activity of the 2nd compound against human mammary cancer cells (MCF-7). FIG. 8 illustrates the activity when tamoxifen is used in combination with the 2nd compound.

FIG. 9 shows an UV absorption spectrum. FIG. 10 shows an EI mass spectrum. FIG. 11 shows an IR absorption spectrum. FIG. 12 shows a proton NMR spectrum. FIG. 13 shows a 13C-NMR spectrum.

FIG. 14 illustrates the growth-inhibiting activity of the 3rd compound against human mammary cancer cells (MCF-7). FIG. 15 illustrates the activity when tamoxifen is used in combination with the 3rd compound.

FIG. 17 shows an IR absorption spectrum of the same compound.

BEST MODE FOR CARRYING OUT THE INVENTION

This invention provides novel androst-4-ene-3,17-dione derivatives having biological activities, and will hereinafter be illustrated in detail by way of examples.

Culture of microorganisms and conversion of substrate by the microorganisms

Acremonium strictum NN106 (Deposit No. FERM P-9143) which is a strain of mold fungi was inoculated on 100 ml of the culture medium composition indicated in Table 1 in a Erlenmeyer flask having a volume of 500 ml. The culture was incubated and shaken simultaneously at 24° C. for 48 hours in a incubator with a rotary shaker.

The above strain was deposited as FERM P-9143 in Fermentation Research Institute of the Agency of Industrial Science and Technology on Jan. 21, 1987.

TABLE 1

| Constituent | (medium composition) Amount (g) |
| --- | --- |
| Malt extract | 30 |
| Peptone | 20 |
| Soybean meal | 10 |
| Potassium phosphate, monobasic | 5 |
| Magnesium sulfate | 5 |
| Purified water | 1,000 ml |

As a substrate androst-4-ene-3,17-dione was dissolved in dimethylformamide in advance so as to obtain a substrate concentration of 50 mg/ml.

After terminating the shaking of the culture, 2 ml of the above substrate solution was added to the culture medium in the Erlenmeyer flask, and then a further cultivation was carried out for 24-48 hours under the same conditions as above.

After completing the reaction, solid matters and cells were removed from the resultant culture solution by filtration or centrifugal separation. The resultant supernatant was extracted three times, each time using one third of its volume of ethyl acetate. The solvent was removed from the extracted solution with a rotary evaporator.

A crude fraction thus obtained was dissolved in chloroform (or methanol) and divided into further fractions with a high performance liquid chromatograph (manufactured by Senshu Science Co.). A silica gel column (20 mm diameter×300 mm length) and a elution solvent (chloroform:methanol=98:2) were used in the chromatography.

A compound in a further divided fraction was identified as androst-4-ene-3,17-dione-6β,11α-diol (the 2nd compound of this invention) by its below described physiological and chemical properties. Another compound contained in a fraction which elutes later, for example, at 45 minutes as compared to 23 minutes for the above 2nd compound was identified as androst-4-ene-3,17-dione-6β,14α-diol (the 3rd compound of this invention).

A novel compound androst-4-ene-3,17-dione-6β,11α-diol which is the 2nd compound of this invention is represented by the chemical formula (II):

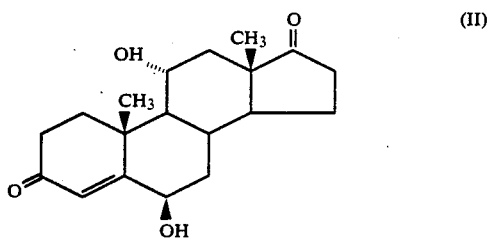
(II)

The compound is identified by the following physiocochemical properties.

Figure 4:
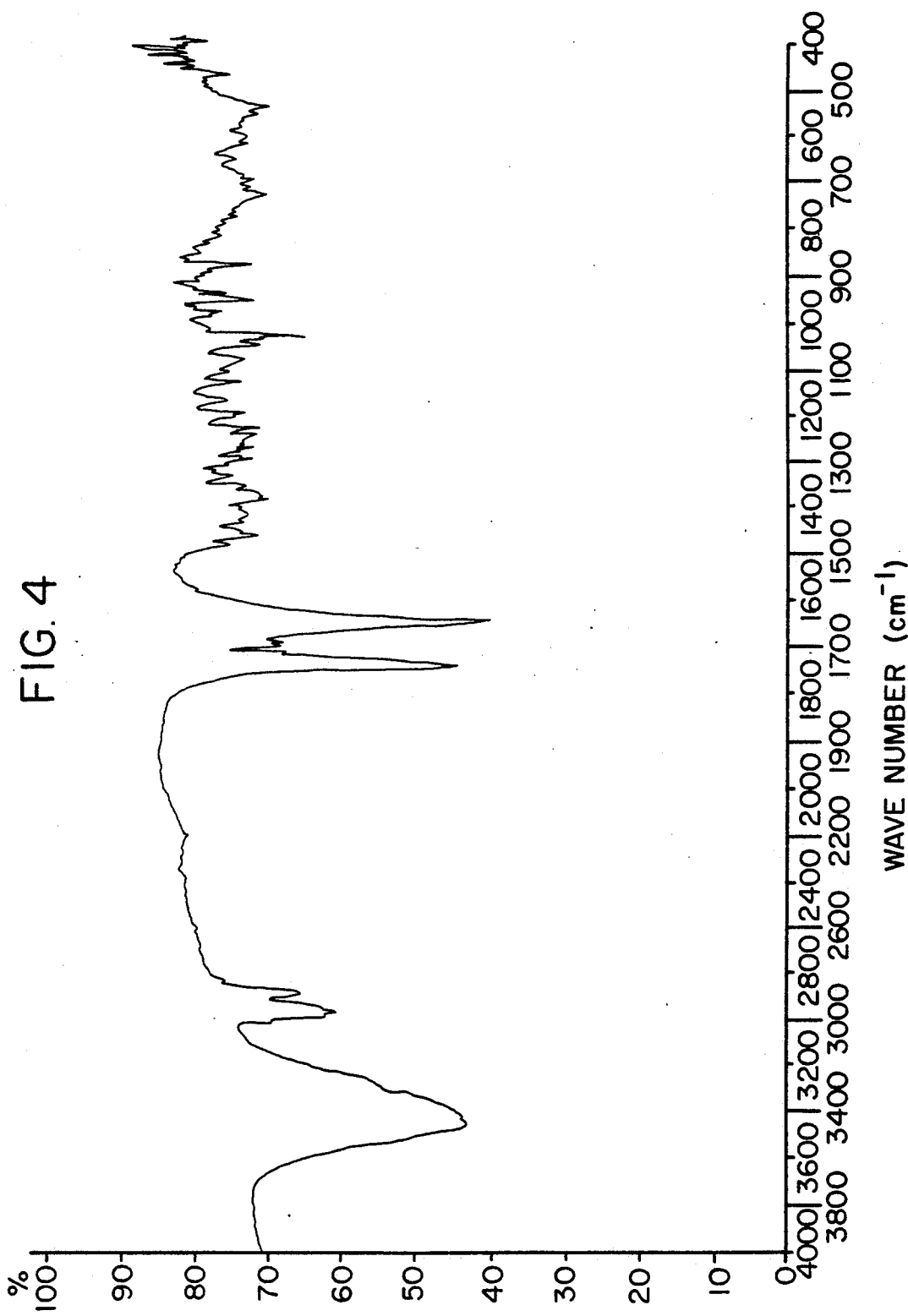
FIGS. 4-8 relate to the 2nd compound of this invention.
Figure 5:
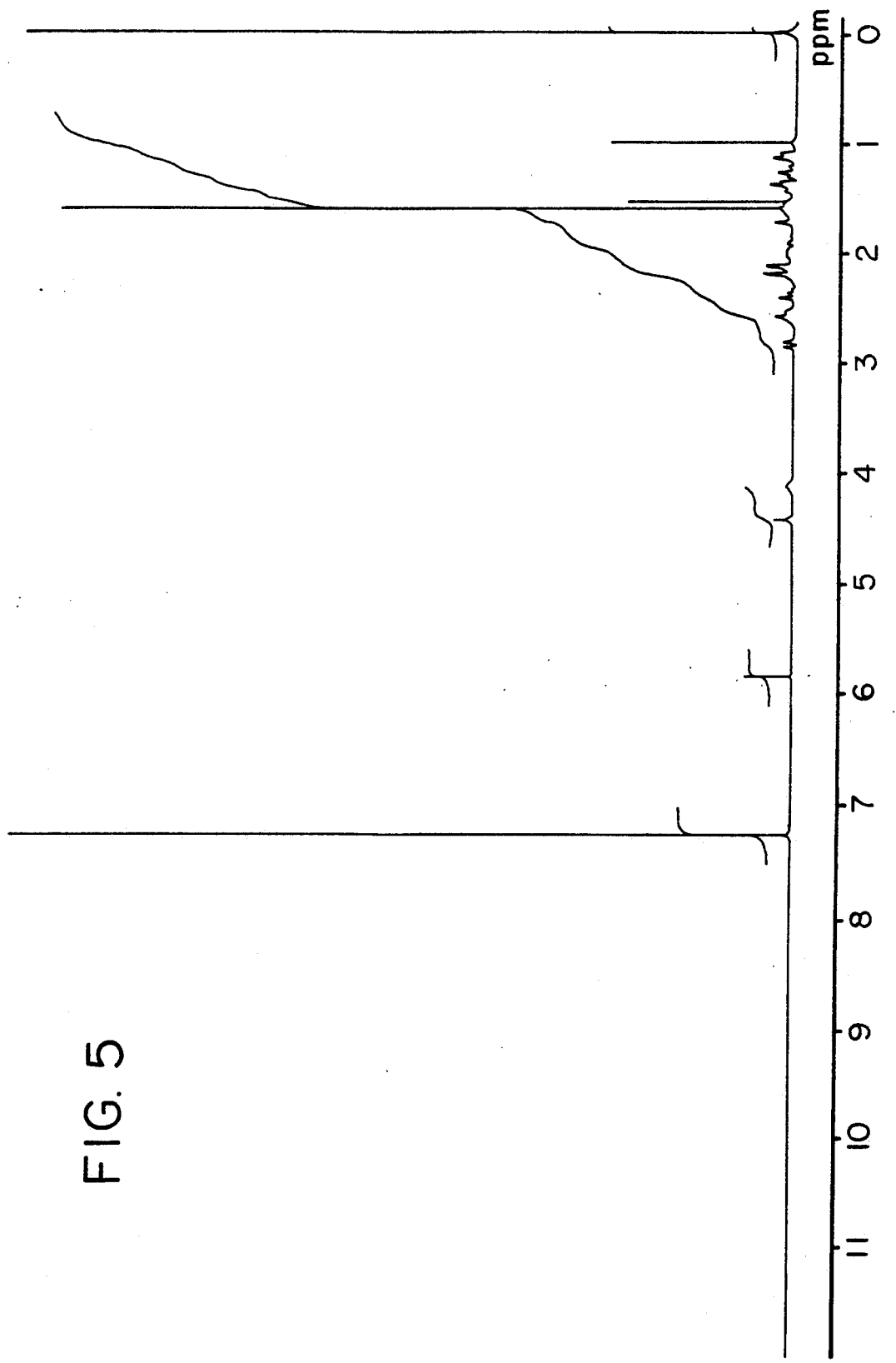
Figure 6:
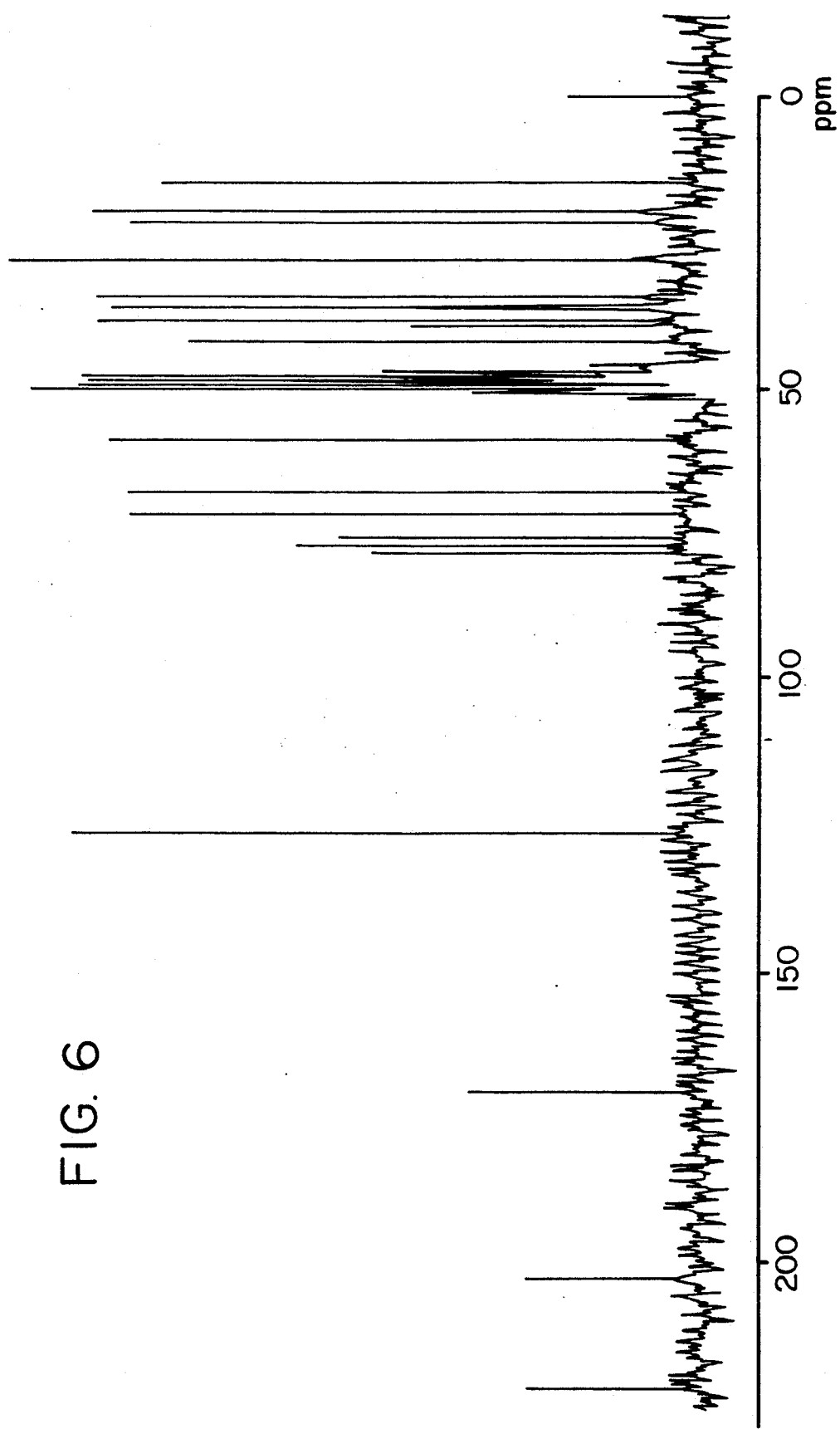

| | | |
|---|---|---|
| (1) | Appearance | White powder |
| (2) | Molecular weight | 318 |
| (3) | Molecular formula | $C_{19}H_{26}O_4$ |
| (4) | Melting point | 278-279° C. |
| (5) | Specific rotation | $[\alpha]D = +34°$ |
| (6) | EI mass spectrum | m/Z = 318 |
| (7) | Infrared absorption spectrum | KBr method. See FIG. 4. 3450, 3400, 2950, 1730, 1640 cm$^{-1}$ |
| (8) | Proton nuclear magnetic resonance spectrum | See FIG. 5 |
| (9) | 13C-Nuclear magnetic resonance spectrum | See FIG. 6 |
| (10) | Solubility | Soluble in ethanol, methanol ethyl acetate and chloroform. Slightly soluble in water and hexane. |

A novel compound androst-4-ene-3,17-dione-6β,14α-diol which is the 3rd compound of this invention is represented by the chemical formula (III):

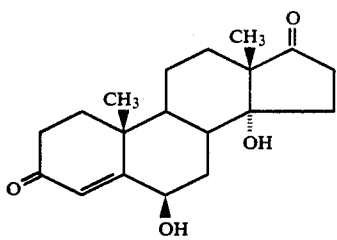
(III)

The compound is identified by the following physiochemical properties.

Figure 9:
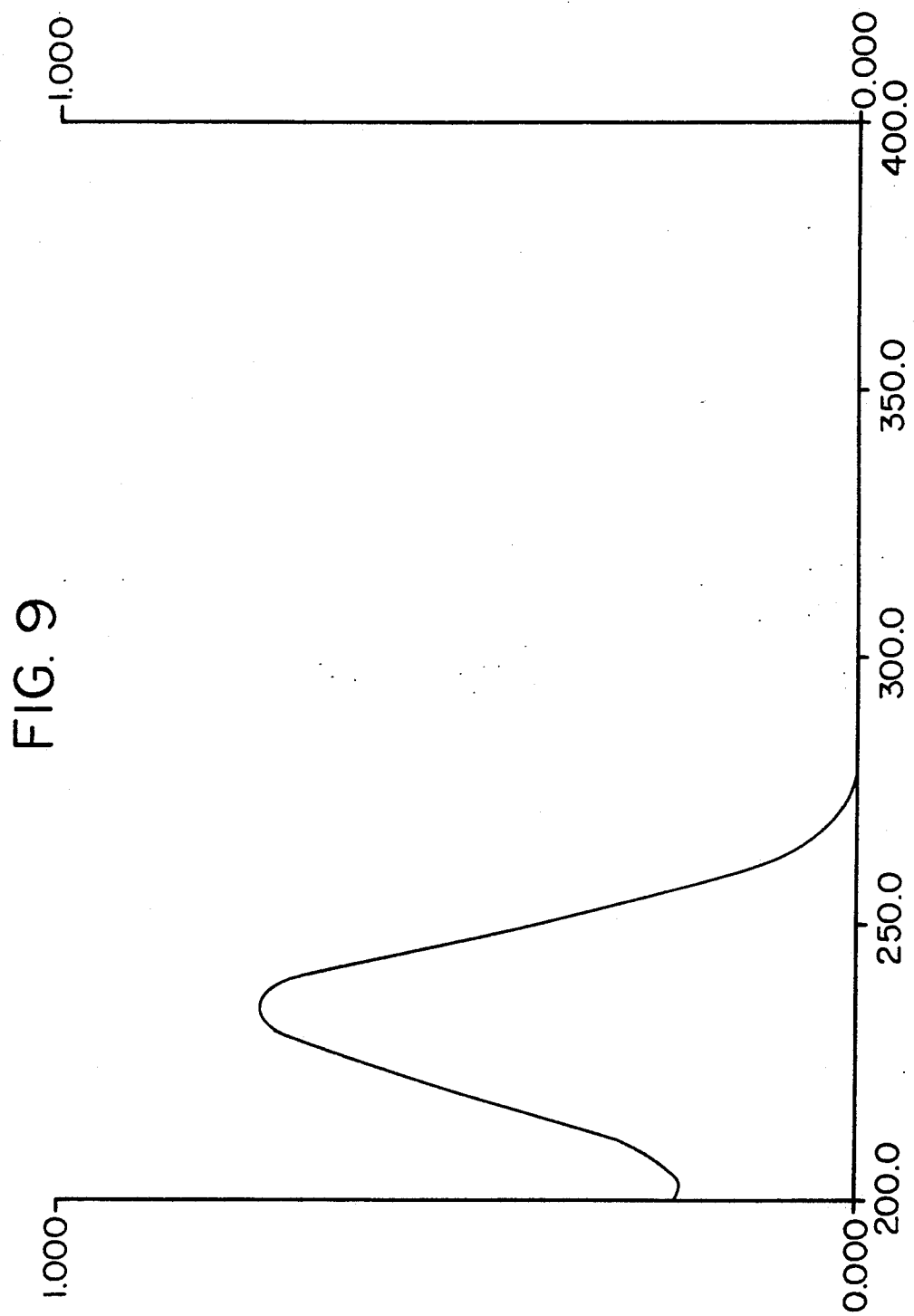
FIGS. 9-15 relate to the 3rd compound of this invention.
Figure 10:
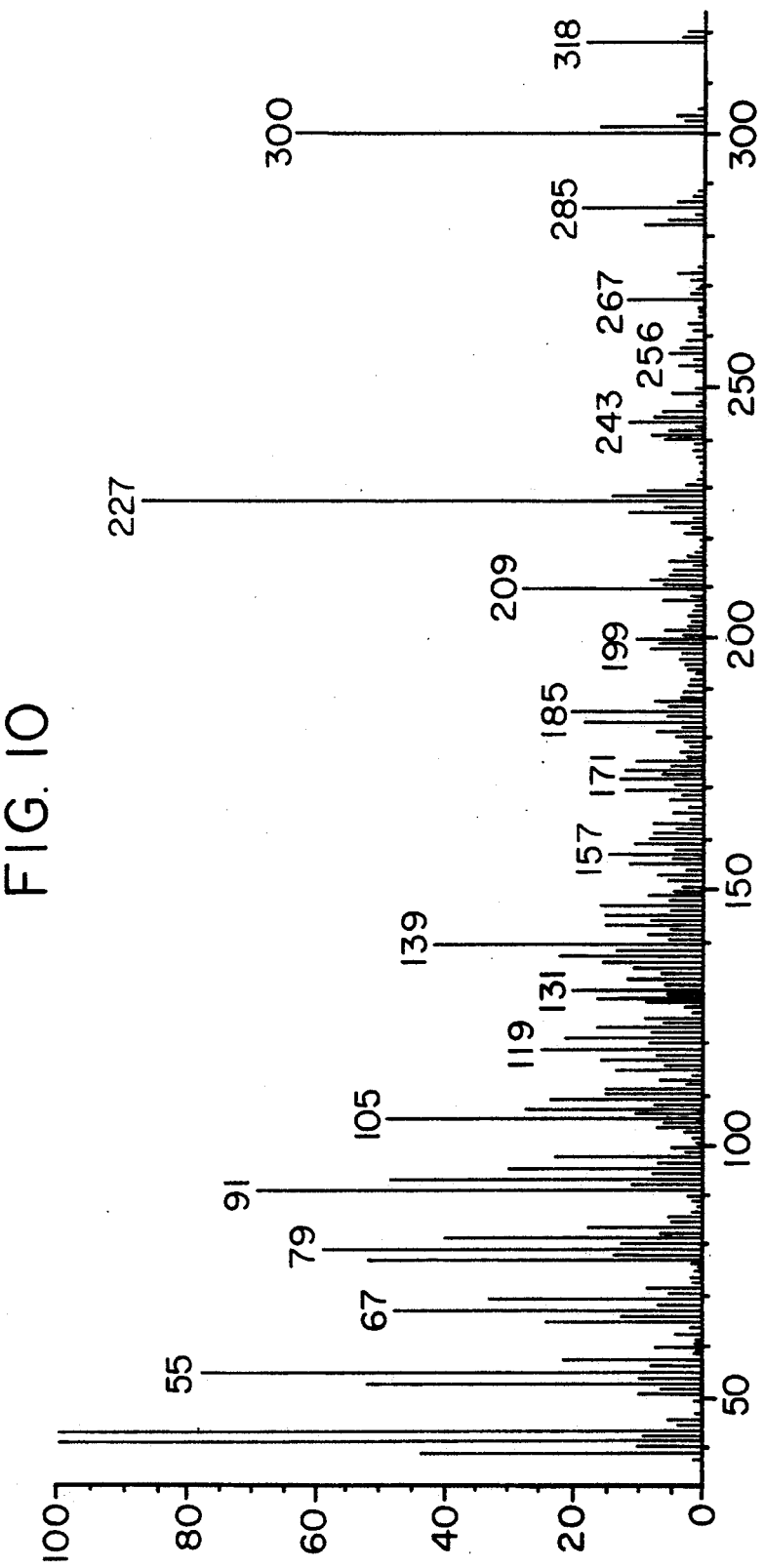
Figure 11:
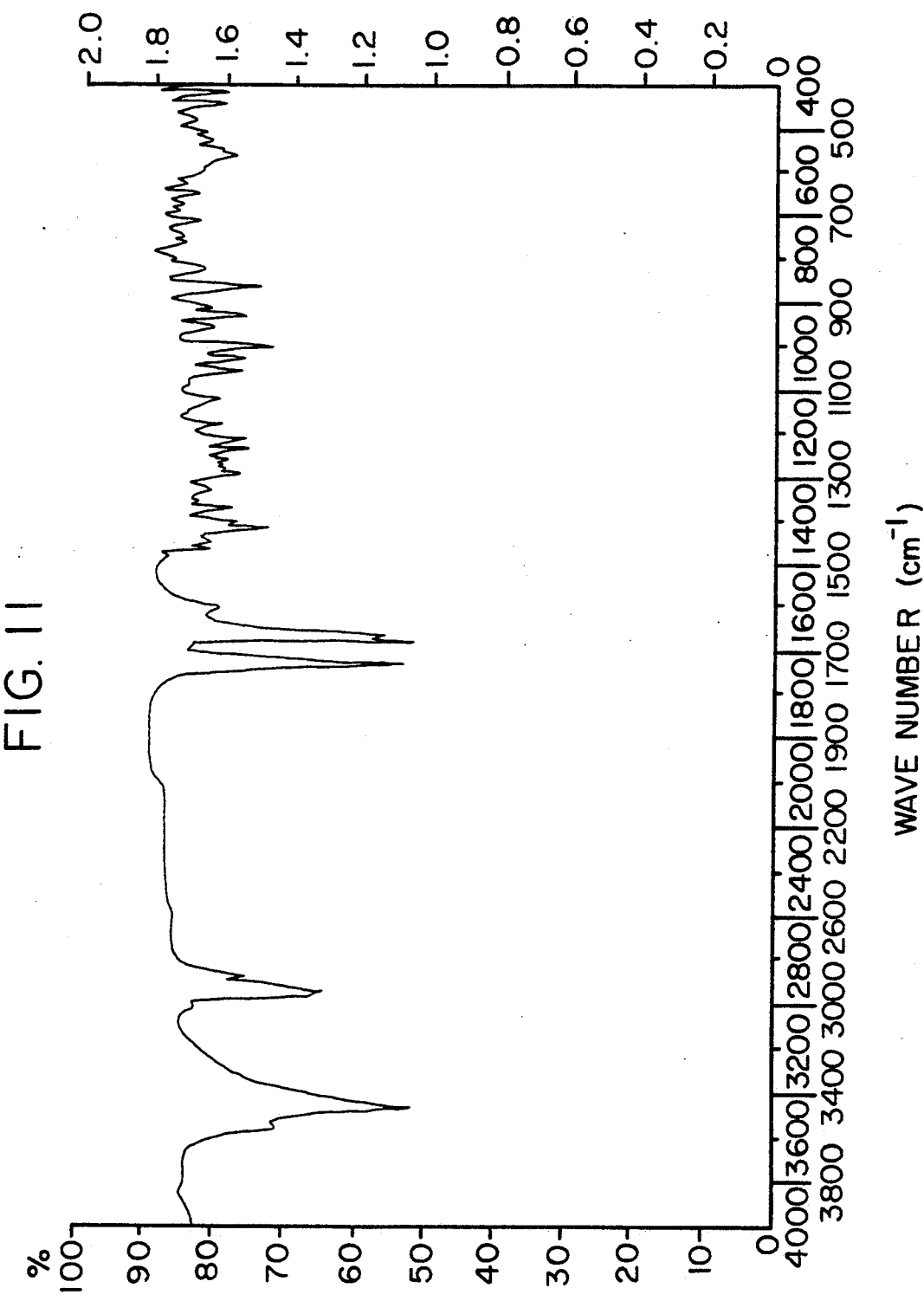
Figure 12:
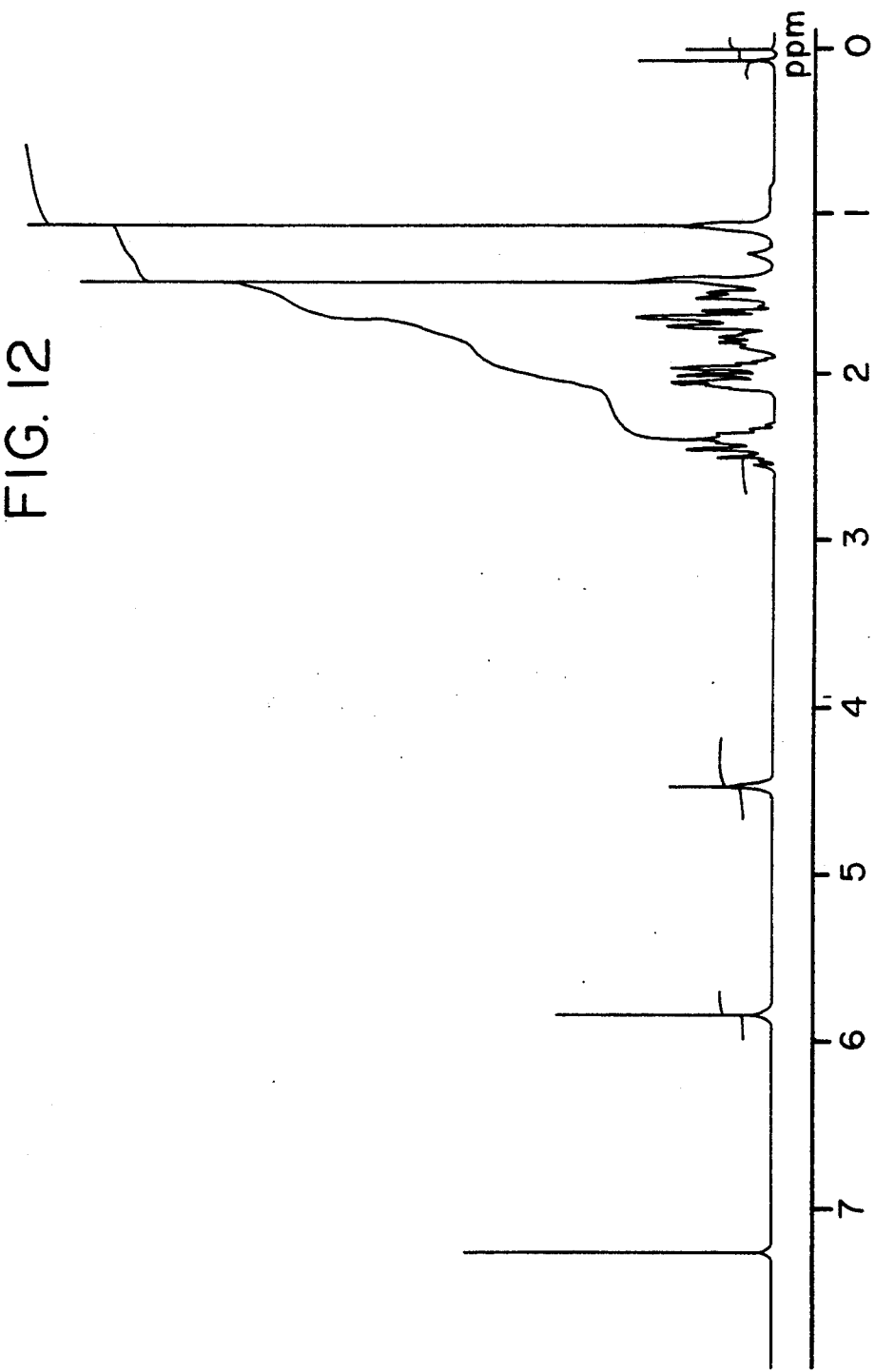
Figure 13:
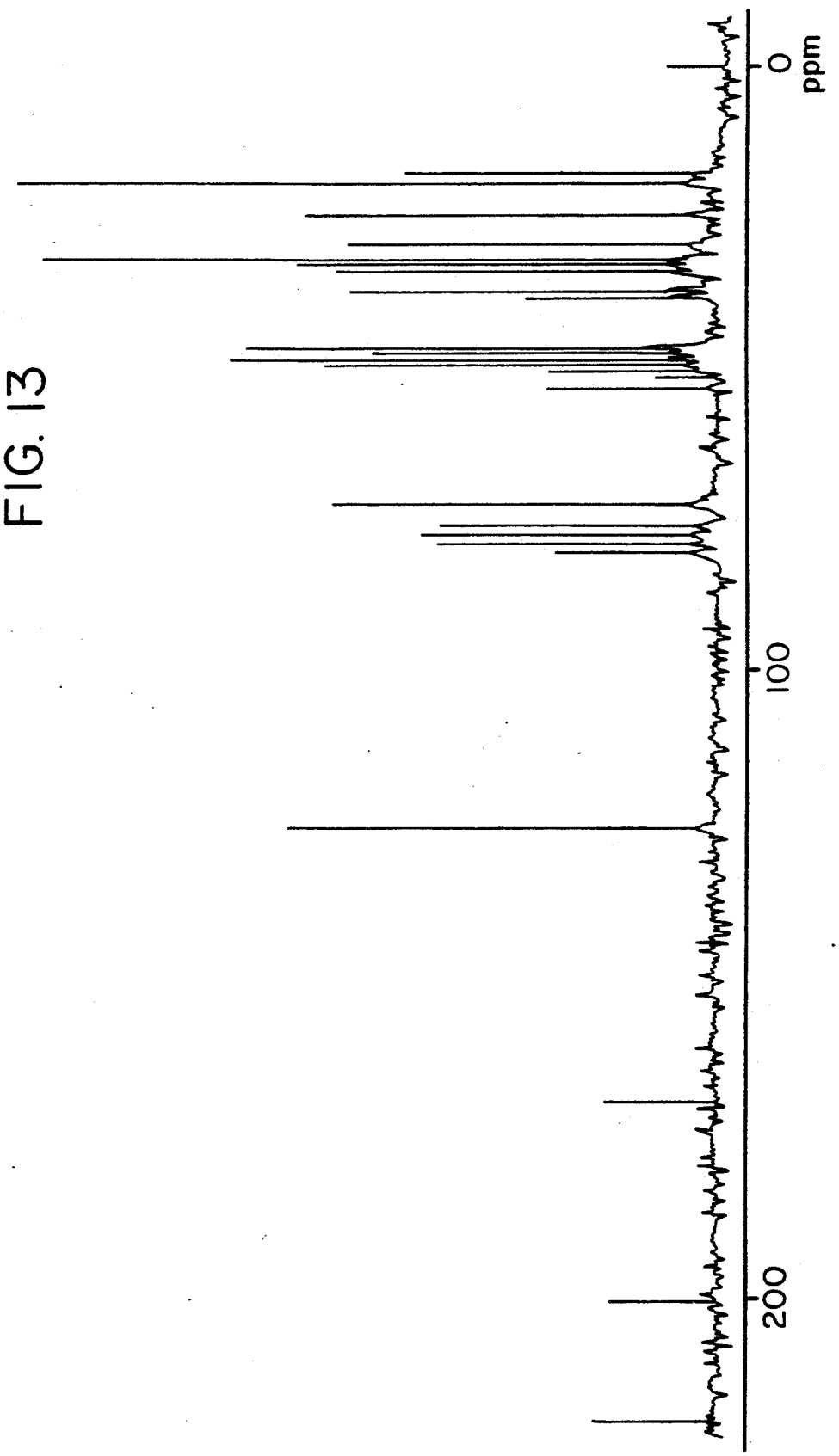

| | | |
|---|---|---|
| (1) | Appearance | White powder |
| (2) | Molecular weight | 318 |
| (3) | Molecular formula | $C_{19}H_{26}O_4$ |
| (4) | Melting point | 256-257° C. |
| (5) | Specific rotation | $[\alpha]D = +104°$ C. (C = 0.1, methanol) |
| (6) | Ultraviolet absorption spectrum | Maximum absorption 236 nm (neutral, in methanol) See FIG. 9. |
| (7) | EI mass spectrum | m/Z = 318, See FIG. 10. |
| (8) | Infrared absorption spectrum | KBr method, See FIG. 11. 3460, 2960, 1748, 1682, 1650 cm$^{-1}$ |
| (9) | Proton nuclear magnetic resonance spectrum | See FIG. 12. |
| (10) | 13C-Nuclear magnetic resonance spectrum | See FIG. 13. |
| (11) | RF value (Developing solvent ... chloroform:methanol = 9:1) | 0.13 |
| (12) | Solubility | Soluble in ethanol, methanol, ethyl acetate and chloroform. Insoluble in water and hexane. |

Preparation of androst-4-ene-3,6,17-trione-14α-ol (the 1st compound of this invention)

In a solution of 100 mg of androst-4-ene-3,17-dione-6β,14α-diol obtained above in 4.8 ml of chloroform, 600 mg of activated manganese dioxide was added and reacted for several hours at room temperature. After completing the reaction, manganese dioxide was filtered and thoroughly washed. The solvent was removed from the filtrate with a rotary evaporator to obtain a crude fraction.

The crude fraction was dissolved in a small amount of chloroform (or methanol) and divided into further fractions with a high performance liquid chromatograph (manufactured by Senshu Science Co.). A silica gel column (20 mm diameter×300 mm) and an elution solvent (chloroform:methanol=98:2) were used in the chromatography. Thus androst-4-ene-3,6,17-trione-14α-ol was eluted to obtain the yield of 40 mg.

The compound is represented by the chemical formula (IV):

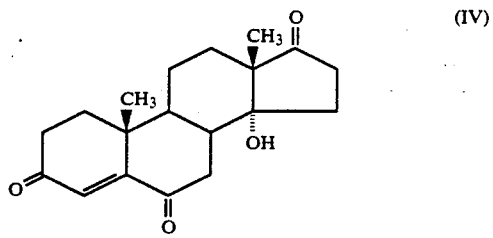
(IV)

The compound is identified by the following physicochemical properties.

Figure 1:
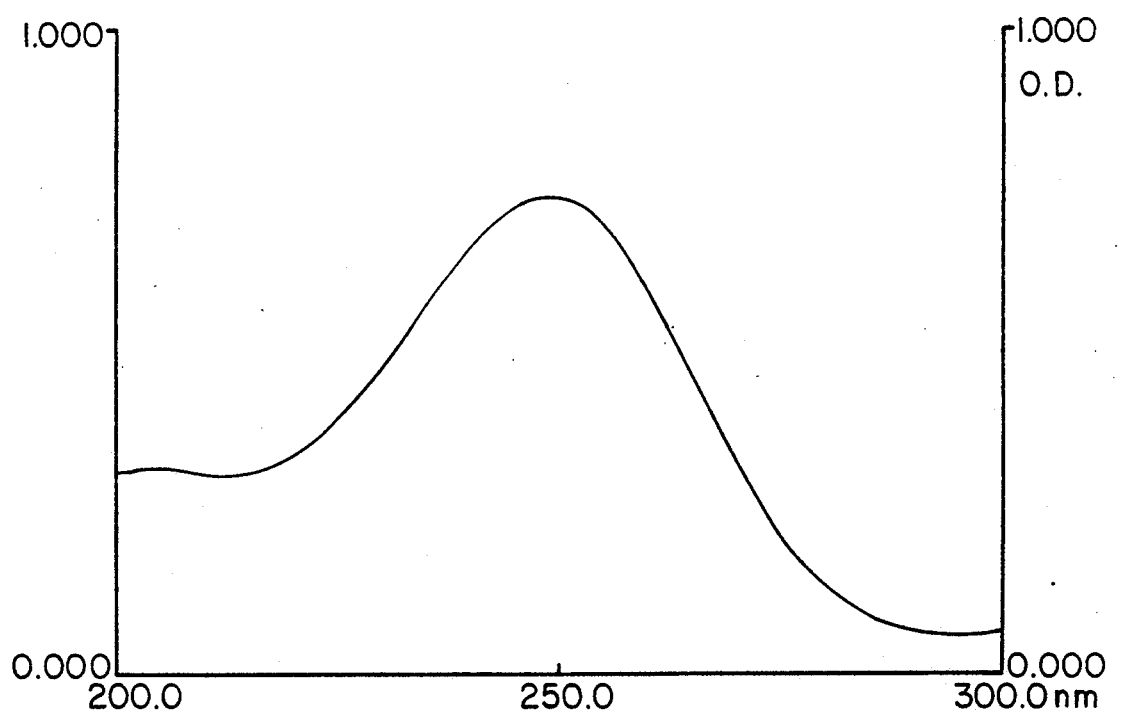
FIGS. 1-3 relate to the 1st compound of this invention.
Figure 2:
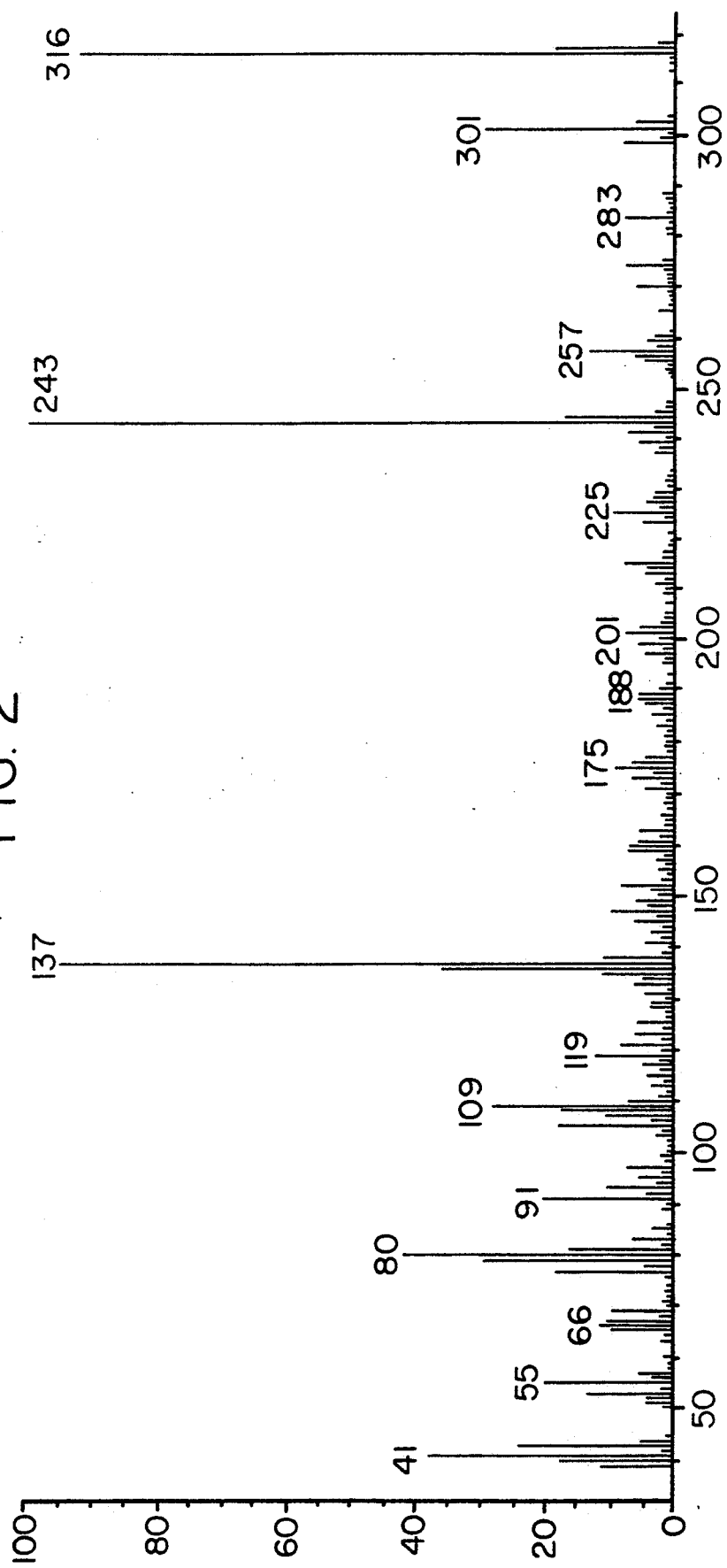
Figure 3:
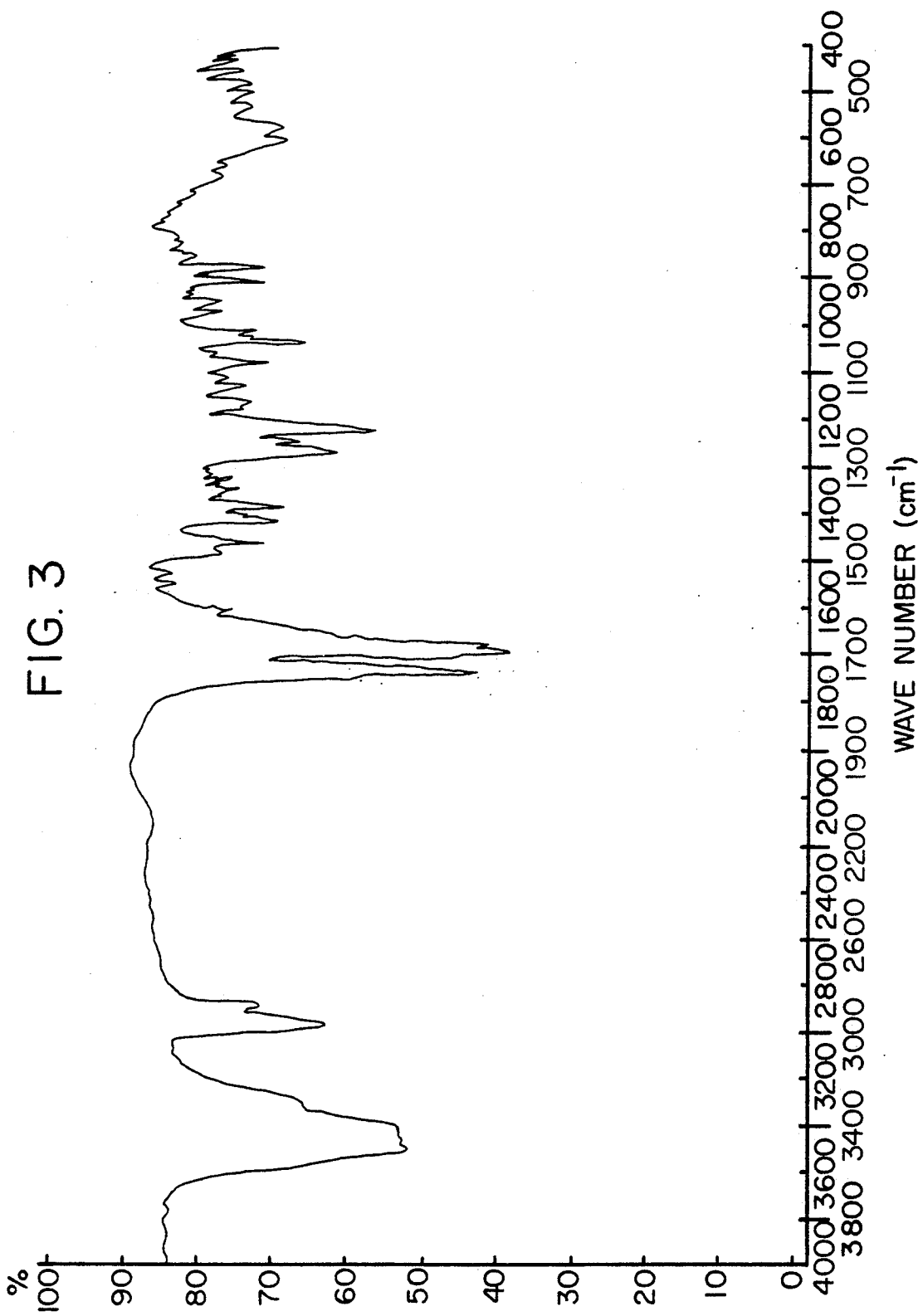

| | | |
|---|---|---|
| (1) | Appearance | White powder |
| (2) | Molecular weight | 316 |
| (3) | Molecular formula | $C_{19}H_{24}O_4$ |
| (4) | Ultraviolet absorption spectrum | See FIG. 1. |
| (5) | EI mass spectrum | m/Z = 316 |
| (6) | Infrared absorption spectrum | KBr method 3520, 3410, 2970, 1735, 1690, 1675, 1605 cm$^{-1}$ See FIG. 3. |
| (7) | RF value (Developing solvent ... chloroform:methanol = 9:1) | 0.43 |
| (8) | Solubility | Soluble in ethanol, methanol, ethyl acetate and chloroform. Insoluble in water and hexane. |

Preparation of position-6 substituted derivatives

Androst-4-ene3,17-dione-6β,14α-diol is dissolved in a solvent such as pyridine. Acetic anhydride, propionic anhydride, isobutyric anhydride or trimethylacetic anhydride is added to the solution and thoroughly stirred for several hours at room temperature. Then water is added to the reaction mixture. The resultant aqueous solution is extracted with ether. The ether extract is dehydrated with anhydrous sodium sulfate and concentrated. The 6-acyl derivatives of androst-4-ene-3,17-dione-6β,14α-diol are obtained as desired products in the yield of about 96%.

These derivatives are novel compounds and represented by the chemical formula (V):

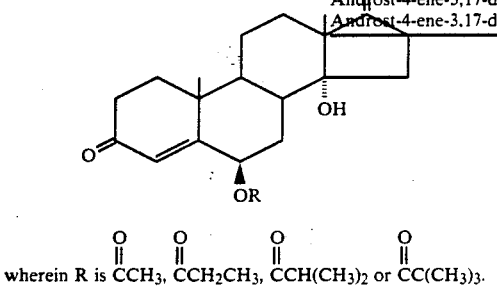

wherein R is $\overset{O}{\underset{\|}{C}}CH_3$, $\overset{O}{\underset{\|}{C}}CH_2CH_3$, $\overset{O}{\underset{\|}{C}}CH(CH_3)_2$ or $\overset{O}{\underset{\|}{C}}C(CH_3)_3$.

Physiological and chemical properties of these compounds are illustrated in Table 2.

expected to be utilized in the medical field with particular application to anticancer drugs.

Therefore the inventors have examined the activity of these compounds.

Method of measurement

According to the method of E. A. Thompson [J. Biol. Chem., 249, 5364–5372 (1974)], aromatase was extracted from human placenta and purified.

The inhibiting effect of test compounds at the concentration of 20 μM was examined by measuring the enzyme activity in the substrate of [1β,2β-3H]androstene-dione.

The results are illustrated in Table 3.

TABLE 3

| Test compounds | | Aromatase activity | Inhibition ratio |
|---|---|---|---|
| Chemical name | (Claim No.) | E₁pmole/min/mg | (%) |
| (Absence) | | 19.70 | 0 |
| Androst-4-ene-3,6,17-trione-14α-ol | (claim 2) | 1.87 | 90.5 |
| Androst-4-ene-3,17-dione-6β,11α-diol | (claim 3) | 13.51 | 31.4 |
| Androst-4-ene-3,17-dione-6β,14α-diol | (claim 4) | 12.46 | 36.8 |
| Androst-4-ene-3,17-dione-6-acetoxy-6β,14α-diol | (claim 5) | 17.09 | 13.2 |
| Androst-4-ene-3,17-dione-6β-propionyloxy-14α-ol | (claim 6) | 16.82 | 14.6 |
| Androst-4-ene-3,17-dione-6β-isobutyryloxy-14α-ol | (claim 7) | 16.83 | 15.6 |
| Androst-4-ene-3,17-dione-6β-trimethylacetoxy-14α-ol | (claim 8) | 15.4 | 21.6 |

Growth-inhibiting activity against human mammary cancer cells

Growth-inhibiting activity against human mammary cancer cells (MCF-7) has been found in vitro on the 2nd and 3rd compounds of this invention. The test results will be illustrated below.

Method of test

Eagle's minimum essential medium containing 5% of bovine fetal serum was placed in a laboratory dish hav-

TABLE 2

Figure 16:
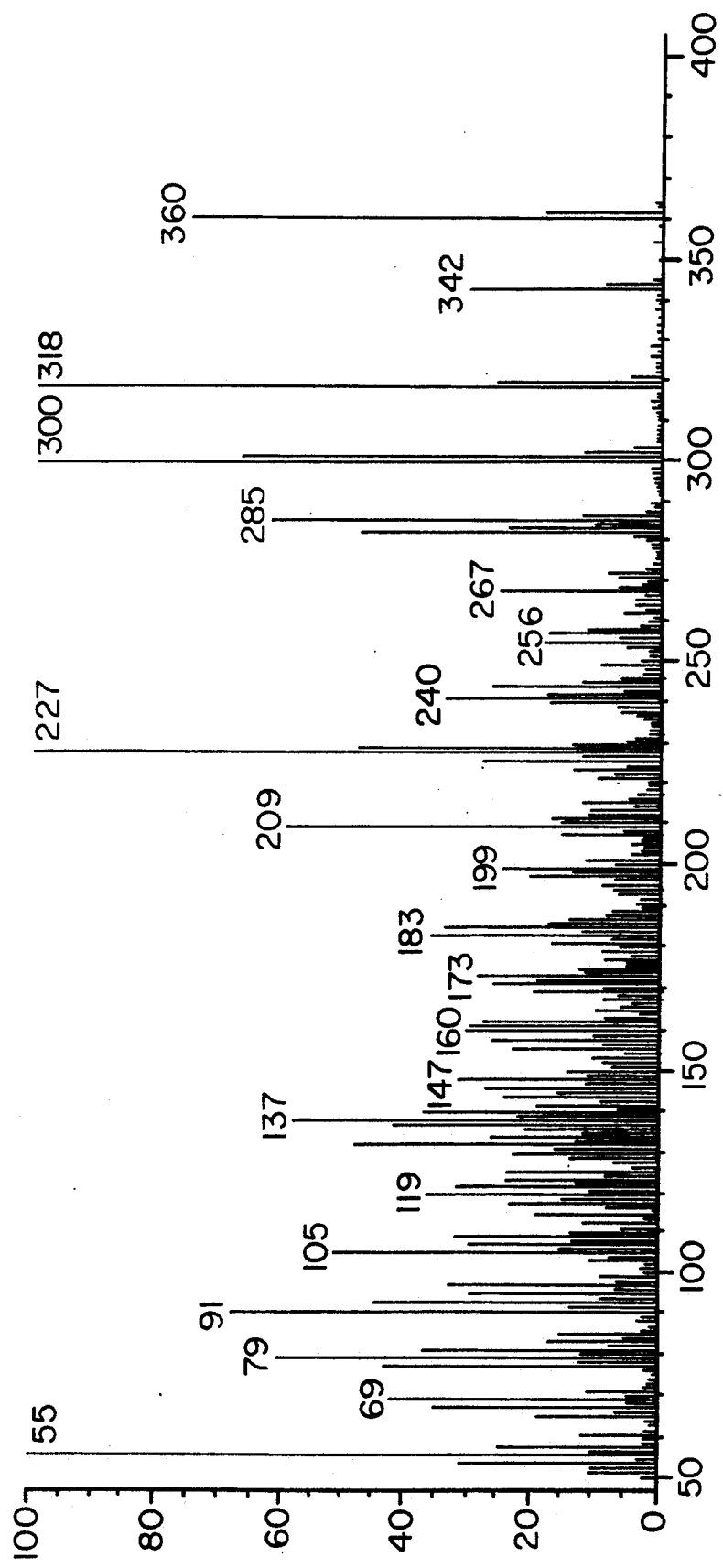
FIG. 16 shows an EI mass spectrum of androst-4-ene-3,17-dione-6β-acetoxy-14α-ol which is the 4th compound of this invention.

| No. | R in formula (V) | Appearance | Mol. weight | Mol. formula | Mp. (°C.) | Spectrum EI mass | Spectrum IR (KBr method) | Solubility |
|---|---|---|---|---|---|---|---|---|
| 1 | $\overset{O}{\underset{\|}{C}}CH_3$ | White powder | 360 | C₂₁H₂₈O₅ | 241~243 | m/Z 360 See FIG. 16 | See FIG. 17 | Soluble in methanol, ethyl acetate, chloroform. Insoluble in water, hexane, petroleum ether. |
| 2 | $\overset{O}{\underset{\|}{C}}CH_2CH_3$ | White powder | 374 | C₂₂H₃₀O₅ | 245 | m/Z 374 | | Soluble in methanol, ethyl acetate, chloroform. Insoluble in water, hexane, petroleum ether. |
| 3 | $\overset{O}{\underset{\|}{C}}CH(CH_3)_2$ | White powder | 388 | C₂₃H₃₂O₅ | 270 | m/Z 388 | | Soluble in methanol, ethyl acetate, chloroform. Insoluble in water, hexane, petroleum ether. |
| 4 | $\overset{O}{\underset{\|}{C}}C(CH_3)_3$ | White powder | 402 | C₂₄H₃₄O₅ | 280 | m/Z 402 | | Soluble in methanol, ethyl acetate, chloroform. Insoluble in water, hexane, petroleum ether. |

INDUSTRIAL APPLICABILITY

Human placenta derived estrogen synthetic enzyme inhibiting activity

The above obtained androsten derivatives of this invention have a biologically inhibiting effect on the activity of human placenta-derived estrogen-synthesizing enzyme (aromatase). Thus these derivatives are ing a diameter of 2 cm. Human mammary cancer cells (MCF-7) had previously been cultured in a similar medium and 1×10⁴ cells were inoculated on this medium. The inoculated medium was cultured at 37° C., for 2 days in 5% CO2 atmosphere and then exchanged with another medium containing a test compound. The exchange was carried out thereafter every two days with other medium containing a test compound. Trypsin treatment was time-dependently conducted during the test period and a number of cells were counted under a microscope to measure the growth of cells.

Figure 7:
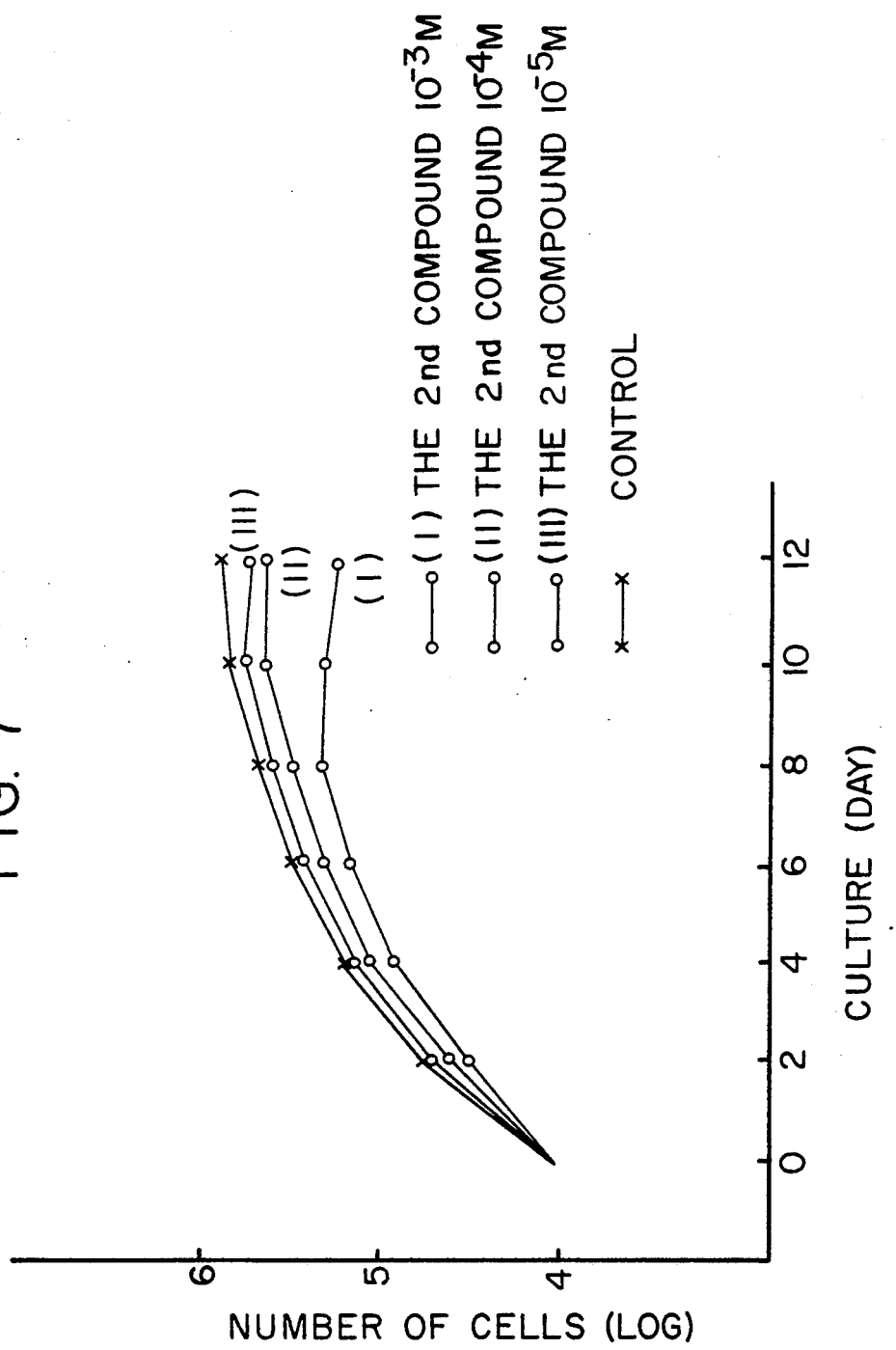
Figure 14:
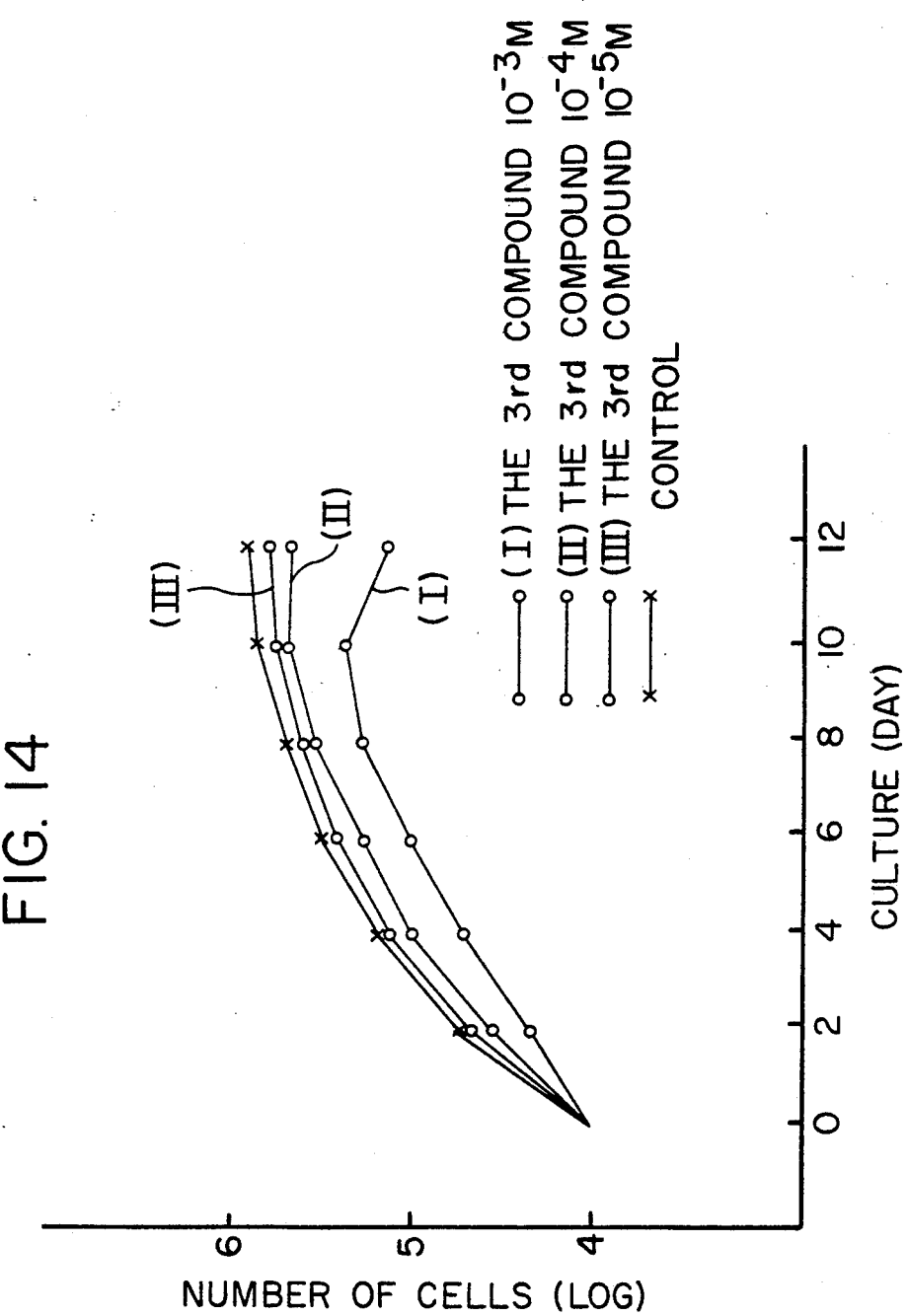

The results are illustrated in FIG. 7 (the 2nd compound of this invention) and FIG. 14 (the 3rd compound of this invention)

Figure 8:
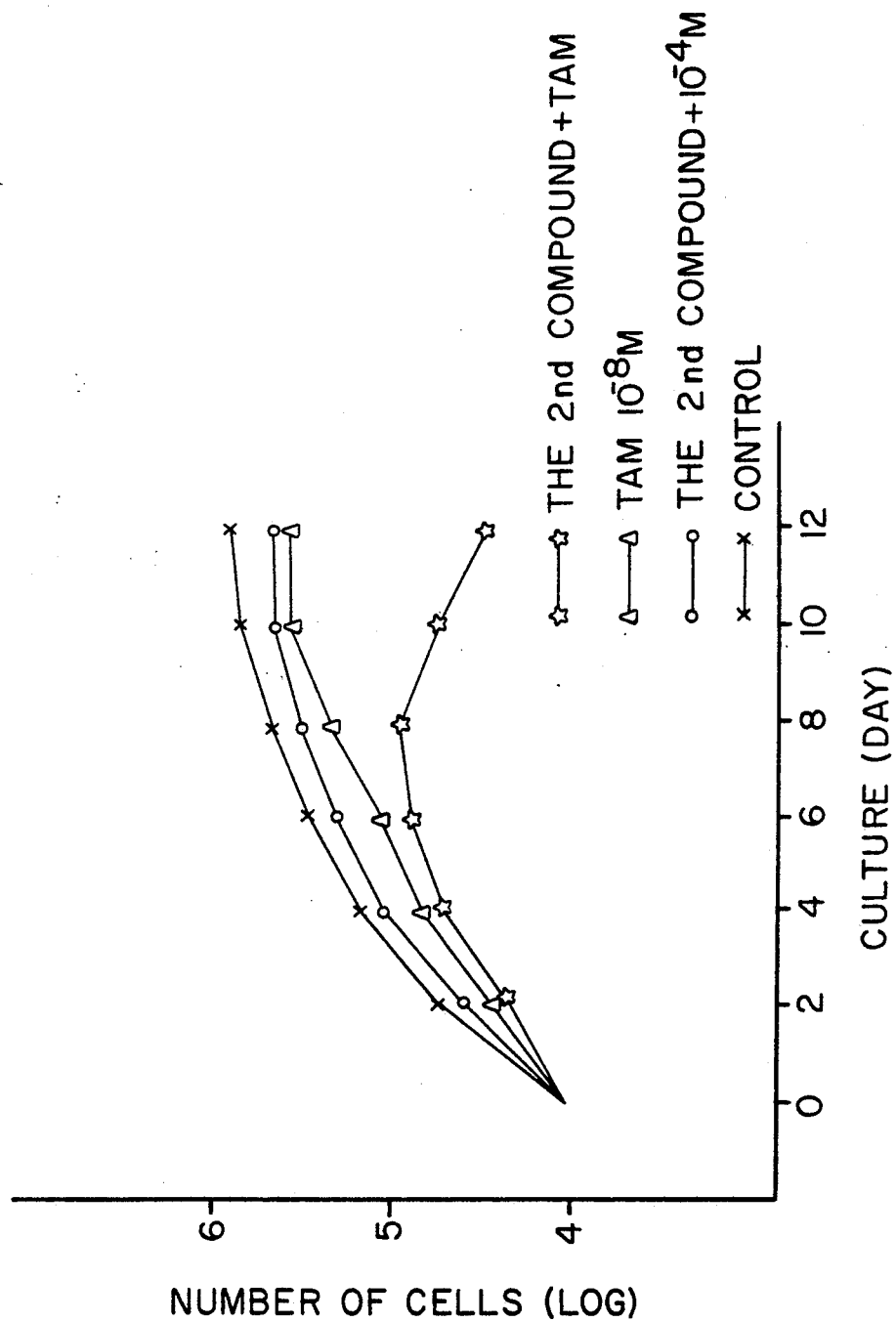
Figure 15:
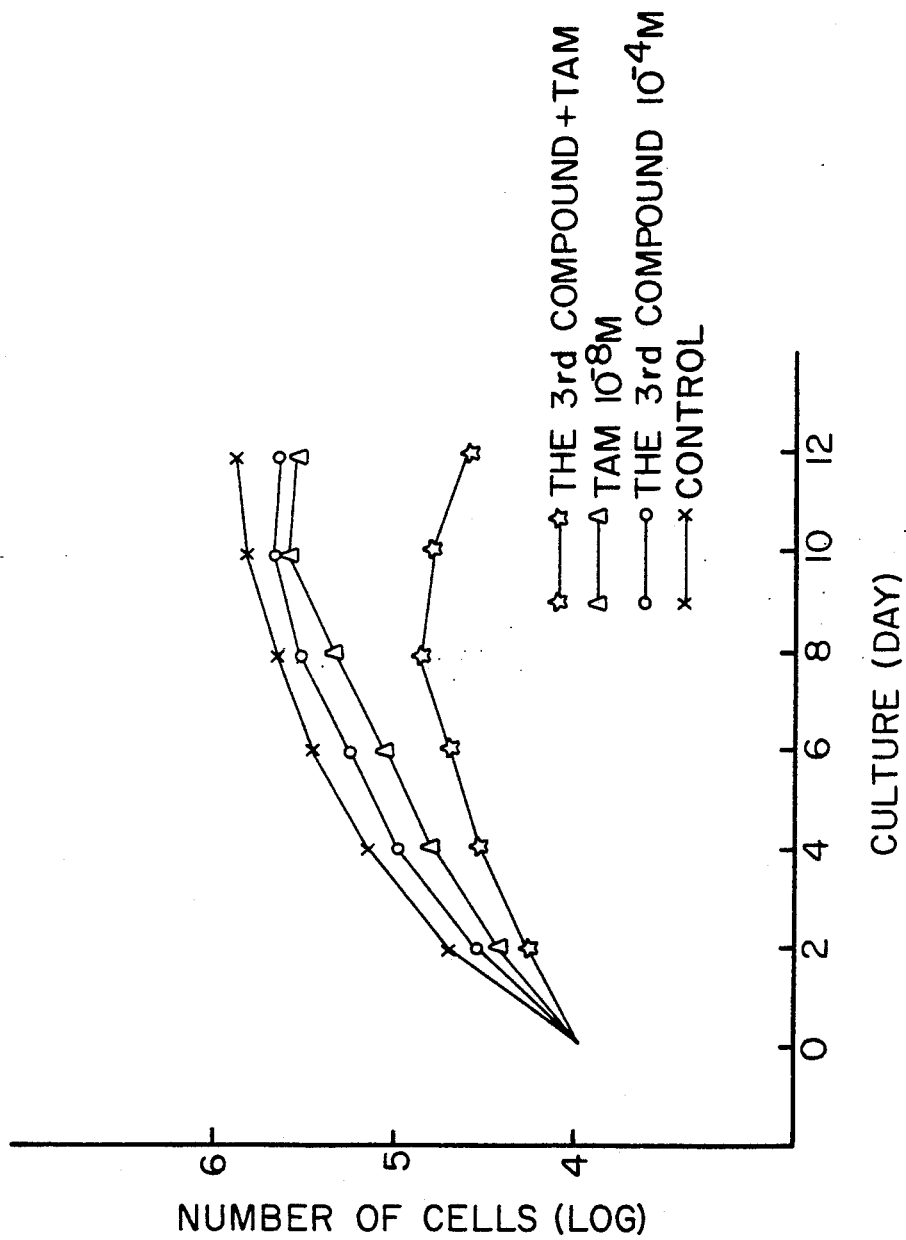

The synergistic effects of these compounds with commercially available tamoxifen (Trade Mark; Nolvatex) which is an anticancer drug were also examined. The effects which have been found are illustrated in FIG. 8 and FIG. 15.

Androgen activity

Androgen activity, although which is comparatively weak, has been found in the 2nd compound of this invention, that is, androst-4-ene-3,17-dione-6$\beta$,11$\alpha$-diol.

Reference to microorganisms deposited pursuant to Regulation 13 bis.
Deposit Organization: Fermentation Research Institute of the Agency of Industrial Science and Technology
Adress: 1-3, Higashi-1-chome, Tsukuba-shi, Ibaraki-ken, JAPAN
Deposit No.: FERM P-9143
Date of Deposit: Jan. 21, 1987

We claim:

1. A novel androst-4-ene-3,17-dione derivative represented by the formula (I):

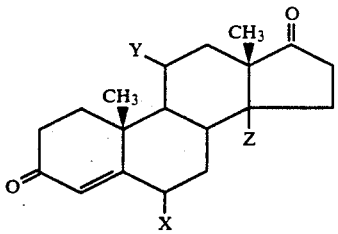

wherein X is =O or $\alpha$H$\beta$OR, Y is 2H or $\alpha$OH$\beta$H, Z is $\alpha$OH, and wherein R is —H, —COCH$_3$, —COCH$_2$CH$_3$, —COCH(CH$_3$)$_2$, or —COC(CH$_3$)$_3$.

2. Androst-4-ene-3,6,17-trione-14$\alpha$-ol, a compound of claim 1.

3. Androst-4-ene-3,17-dione--6$\beta$,14$\alpha$-diol, a compound of claim 1.

4. Androst-4-ene-3,17-dione-6$\beta$-acetoxy-14$\alpha$-ol, a compound of claim 1.

5. Androst-4-ene-3,17-dione-6$\beta$-propionyloxy-14$\alpha$-ol, a compound of claim 1.

6. Androst-4-ene-3,17-dione-6$\beta$-isobutyryloxy-14$\alpha$-ol, a compound of claim 1.

7. Androst-4-ene-3,17-dione-6$\beta$-trimethylacetoxy-14$\alpha$-ol, a compound of claim 1.

* * * * *